United States Patent
Kusuzawa

(10) Patent No.: US 7,349,084 B2
(45) Date of Patent: Mar. 25, 2008

(54) PARTICLE DIAMETER MEASURING APPARATUS

(75) Inventor: Hideo Kusuzawa, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 449 days.

(21) Appl. No.: 10/926,096

(22) Filed: Aug. 26, 2004

(65) Prior Publication Data

US 2005/0046840 A1 Mar. 3, 2005

(30) Foreign Application Priority Data

Aug. 28, 2003 (JP) .............................. 2003-209376

(51) Int. Cl.
*G01N 15/02* (2006.01)
(52) U.S. Cl. ...................... 356/335; 356/336
(58) Field of Classification Search ................ 356/335, 356/336
See application file for complete search history.

(56) References Cited

U.S. PATENT DOCUMENTS

| 5,168,157 A | 12/1992 | Kimura et al. |
| 5,471,298 A | 11/1995 | Moriya |
| 5,721,433 A | 2/1998 | Kosaka |
| 6,999,171 B2 * | 2/2006 | Kusuzawa ................. 356/336 |
| 2003/0030803 A1 * | 2/2003 | Kusuzawa ................. 356/336 |

FOREIGN PATENT DOCUMENTS

| EP | 1 286 152 A1 | 2/2003 |
| JP | 4251212 | 9/1992 |
| JP | 05-273110 A | 10/1993 |
| JP | 08-136439 A | 5/1996 |

* cited by examiner

*Primary Examiner*—Roy M Punnoose
(74) *Attorney, Agent, or Firm*—Birch, Stewart, Kolasch & Birch, LLP

(57) ABSTRACT

A particle diameter measuring apparatus includes a dark field illumination section which dark-field-illuminates particles to be subjected to measurement, an image pickup section which captures a particle image of each of the dark-field-illuminated particles, and a computing section which calculates a particle diameter of each particle based on luminance of the captured image.

19 Claims, 7 Drawing Sheets

PARTICLE DIAMETER MEASURING APPARATUS

CROSS-REFERENCE TO RELATED APPLICATIONS

This application is related to Japanese patent application No.2003-209376 filed on Aug. 28, 2003, whose priority is claimed under 35 USC § 119, the disclosure of which is incorporated by reference in its entirety.

BACKGROUND OF THE INVENTION

1. Field of the Invention

The present invention relates to a particle diameter measuring apparatus and, particularly, to an apparatus for optically measuring a particle diameter.

2. Description of the Related Art

The following apparatuses are known as prior art apparatuses related to the present invention.

An apparatus comprising: a laser light source; a coherence reducing element which receives laser light emitted from the laser light source, reduces the coherence of the laser light and projects the laser light having reduced coherence; a light ring forming section which converts the light projected from the coherence reducing element into ring light; an internal reflection mirror which concentrates the ring light on a particle to be subjected to measurement and illuminates the particle; an objective lens which receives light scattered from the illuminated particle inside the ring light; a light receiving element which receives the scattered light through the objective lens; and a computing section which calculates the diameter of the particle on the basis of the intensity of the scattered light received by the light receiving element from a monotonously increasing function (see, for example, EP 1286152 A1).

An apparatus comprising: a sheath flow cell which transforms a particle suspension liquid flow into a narrow or flat flow surrounded by a sheath liquid; light emitting means which illuminates particles in the transformed suspension liquid flow; image pickup means which captures images of the illuminated particles; image analyzing means which analyzes the captured particle images; and display means; wherein the image analyzing means comprises calculating means which obtains data of the particles by measuring the area and perimeter of each of the captured particle images and calculates the diameter and circularity of each of the particles on the basis of the particle data, graph preparing means which prepares a histogram on the basis of particle size frequency data of the particle diameter, prepares a two-dimensional scattergram based on two parameters corresponding to the particle diameter and the circularity and causes the display means to display the histogram and the scattergram, storage means which stores the captured particle images, and particle image recalling means which causes the display means to collectively display the particle images stored in the storage means (see, for example, U.S. Pat. No. 5,721,433).

In recent years, there has been a demand for measurement of particles each having a diameter on a submicron order to the order of several tens of nanomicrons for precisely analyzing solid constituents of blood and urine, inorganic particles such as fine ceramic particles, pigment particles, cosmetic particles, toner particles and abrasive particles, and organic particles such as food additive particles. However, the prior art apparatuses are unsatisfactory in the accuracy of the measurement of such fine particles.

SUMMARY OF THE INVENTION

The scope of the present invention is defined solely by the appended claims, and is not affected to any degree by the statements within this summary.

A first particle diameter measuring apparatus embodying the present invention comprises: a dark field illumination section which dark-field-illuminates particles; an image pickup section which captures a particle image of each of the dark-field-illuminated particles; and a computing section which calculates a particle diameter of each particle based on luminance of the captured particle image.

A second particle diameter measuring apparatus embodying the present invention comprises: a dark field illumination section which dark-field-illuminates particles; a first image pickup device which captures a particle image of each of the dark-field-illuminated particles; a first computing section which calculates a particle diameter of each particle on the basis of luminance of the particle image captured by the first image pickup device; a bright field illumination section which bright-field-illuminates the particles; a second image pickup device which captures a particle image of each of the bright-field-illuminated particles; and a second computing section which calculates the particle diameter on the basis of a morphological characteristic of the particle image captured by the second image pickup device.

A third particle diameter measuring apparatus embodying the present invention comprises: a light source for illuminating particles; a first filter provided in a light path extending from the light source to the particles for blocking light of a predetermined wavelength traveling along and around an optical axis thereof; first optical means which illuminates the particles with light passing through the first filter and with light traveling outside the first filter; second optical means which divides light from the illuminated particles into two light components; a first image pickup device which captures a particle image of each of the particles by one of the light components divided by the second optical means; a second image pickup device which captures a particle image of each of the particles by the other light component divided by the second optical means; and a second filter disposed in a light path extending between the second optical means and the first image pickup device and transmitting only the light of the predetermined wavelength.

DESCRIPTION OF THE PREFERRED EMBODIMENTS

Terms to be used in embodiments of the present invention will first be defined as follows.

Figure 1:
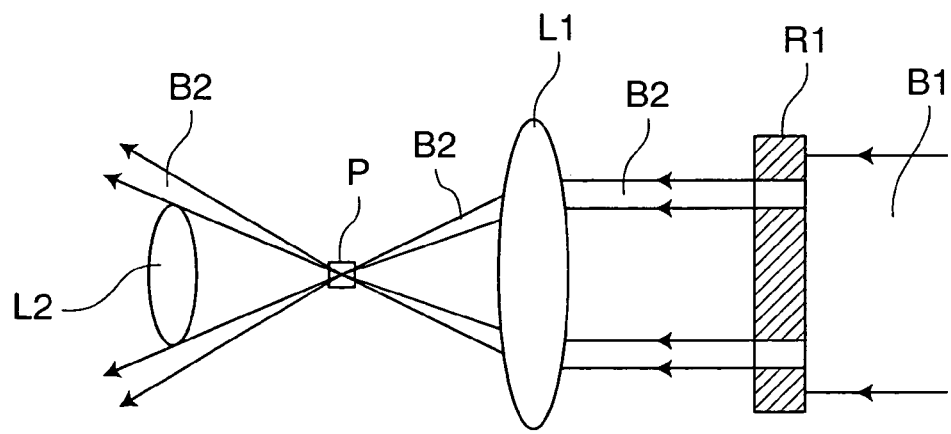
FIG. 1 is a diagram for explaining dark field illumination.

The term "dark field illumination" herein means illumination which is provided for an object P through a restrictor R1 and a condenser lens L1 by collimated illumination light B1, as shown in FIG. 1. That is, the restrictor R1 has a round light blocking plate at its center and an annular opening provided around the light blocking plate. The restrictor R1 restricts the collimated illumination light B1 to be converted into light B2 having a ring shaped cross section and the light B2 is condensed on the object P through the condenser lens L1, where the center light blocking area of the restrictor R1 is equalized with the numerical aperture of an objective lens L2. Thus, illumination light incident on the objective lens L2 is completely eliminated, so that the object P is highlighted in a dark field when viewed from the side of the objective lens L2.

Figure 2:
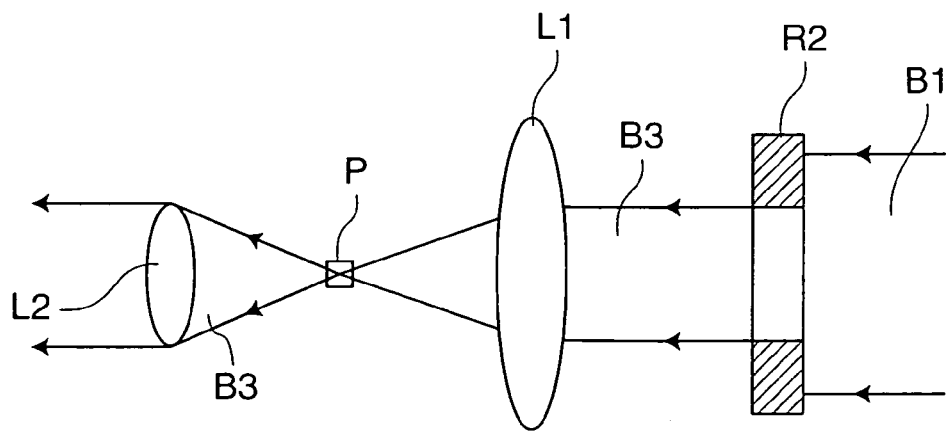
FIG. 2 is a diagram for explaining bright field illumination.

On the other hand, the term "bright field illumination" herein means illumination which is provided for the object P through a restrictor R2 and the condenser lens L1 by the collimated illumination light B1, as shown in FIG. 2. That is, the restrictor R2 has a round opening at its center. The restrictor R1 restricts the collimated illumination light B1 to be converted into illumination light B3 having a light path diameter smaller than the light B1 and the light B3 is condensed on the object P through the condenser lens L1, where the center opening area of the restrictor R2 is equalized with the numerical aperture of the objective L2. Thus, the illumination light does not travel outside the objective lens L2, so that the illumination can effectively be achieved.

First Embodiment

Figure 3:
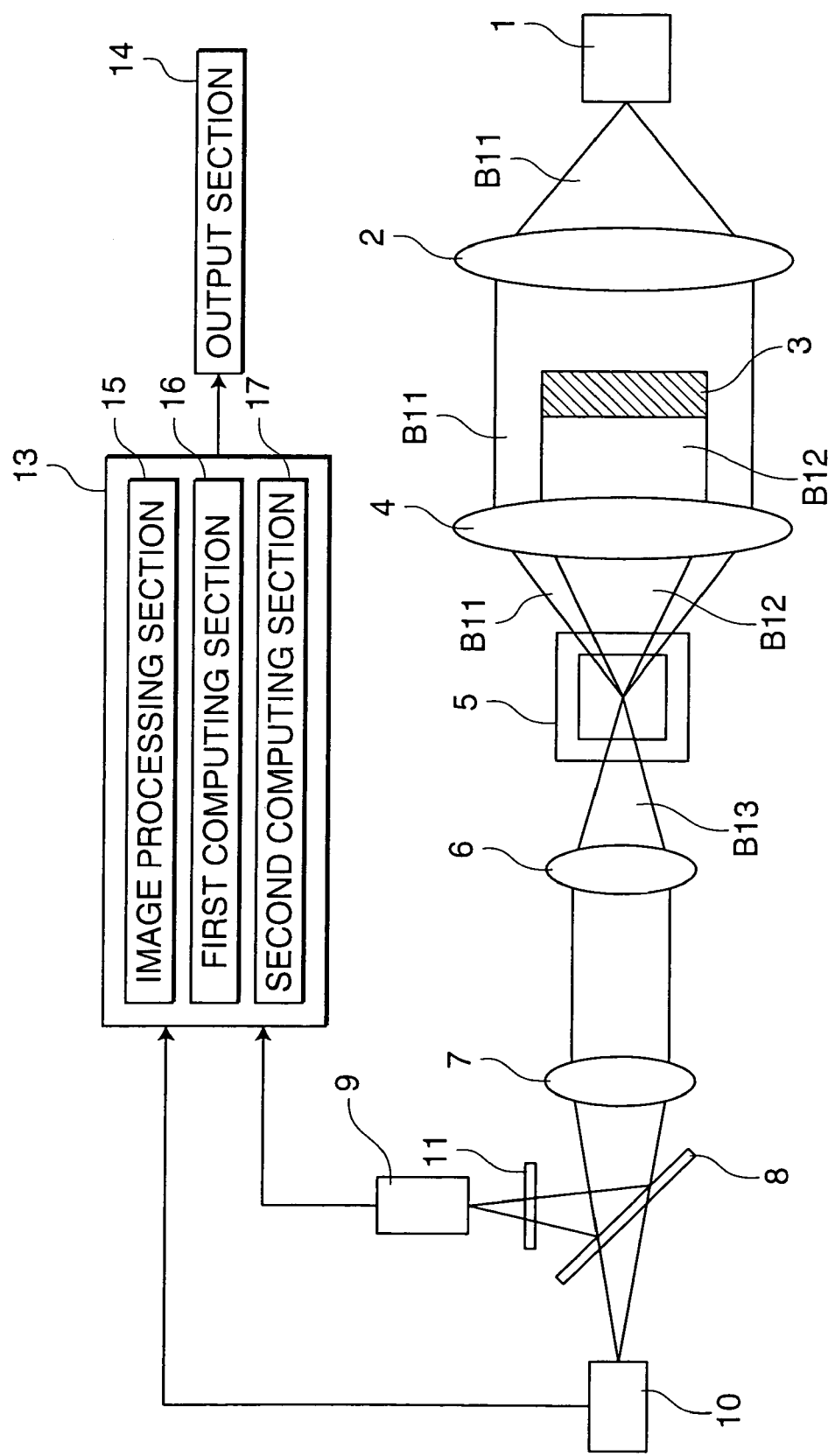
FIG. 3 is a diagram illustrating a construction according to a first embodiment.

FIG. 3 is a diagram illustrating the construction of a particle diameter measuring apparatus according to a first embodiment. As shown, the particle diameter measuring apparatus according to this embodiment includes a flow cell 5 through which a suspension liquid containing particles to be subjected to measurement flows perpendicularly to the paper face of the drawing, an illumination system provided on the right side of the flow cell 5, and an image pickup system provided on the left side of the flow cell 5.

The illumination system on the right side includes a strobe lamp 1 provided as a light source which emits light containing infrared light and visible light, a collimator lens 2, a disk-shaped filter 3 which blocks infrared light and transmits visible light, and a condenser lens 4. The illumination system further includes a driving power source (not shown) for driving the strobe lamp 1, and a control section (not shown) for controlling the driving power source to control the light emitting cycle of the strobe lamp 1. The filter 3 is disposed coaxially with the optical axis of the illumination system between the collimator lens 2 and the condenser lens 4 so as to block infrared light traveling along and around the optical axis.

The image pickup system on the left side includes an objective lens 6, a condenser lens 7, a dichroic mirror 8 which reflects infrared light and transmits visible light, a filter 11 which transmits only infrared light, a first camera 9 which receives the infrared light passing through the filter 11, and a second camera 10 which receives the visible light passing through the dichroic mirror 8.

The first and second cameras 9, 10 each comprise a CCD camera. Image signals outputted from the first and second cameras 9, 10 are inputted into information processing section 13 and processed, and the result of the processing is outputted to an output section 14.

The information processing section 13 includes an image processing section 15 which processes captured images, and first and second computing sections 16 and 17 which respectively perform computing operations on image data obtained by the first and second cameras 9 and 10. The information processing section 13 comprises, for example, a personal computer, and includes at least a CPU and a memory.

An explanation will be given to an image pickup operation to be performed in the apparatus.

When the suspension liquid containing the particles to be subjected to the measurement is caused to flow through the flow cell 5, the control section controls driving electric power from the driving power source to cause the strobe lamp 1 to emit light in a predetermined cycle. The light B11 emitted from the strobe lamp 1 is converted into parallel light by the collimator lens 2.

The filter 3 blocks infrared light traveling along and around the optical axis and transmits only visible light B12 out of the parallel light. The condenser lens 4 concentrates light traveling outside the filter 3 (i.e., light B11 containing infrared light and visible light) on the flow cell 5, so that the particles flowing through the flow cell 5 are dark-field-illuminated against the objective lens 6.

Further, the condenser lens 4 concentrates light passing through the filter 3 (i.e., the visible light B12) on the flow cell 5, so that the particles flowing through the flow cell 5 are bright-field-illuminated against the objective lens 6. Light B13 containing infrared light and visible light from the particles is incident on the condenser lens 7 through the objective lens 6.

The infrared light out of the light from the condenser lens 7 is reflected on the dichroic mirror 8, and passes through the filter 11 to be incident on the first camera 9. That is, only the infrared light from the particles dark-field-illuminated with the light B11 is incident on the first camera 9. Therefore, the first camera 9 captures a dark field illumination image of the particles.

The visible light out of the light from the condenser lens 7 passes through the dichroic mirror 8 to be incident on the second camera 10.

That is, the particles are dark-field-illuminated with the visible light out of the light B11, and bright-field illuminated with the visible light B12. Therefore, both the visible light of the dark field illumination and the visible light of the bright field illumination are incident on the second camera 10. However, the light resulting from the dark-field-illumination of the particles is generally much smaller in intensity than the light resulting from the bright-field-illumination of the particles, so that the second camera 10 virtually captures a bright field illumination image of the particles.

Next, a process for processing the data of the image captured by the first camera 9 will be described with reference to a flow chart shown in FIG. 4.

A dark field illumination image of the particles is first captured by the first camera 9. Then, the captured dark field illumination image is converted into a luminance reversion image, which is in turn stored together with the dark field illumination image in the memory of the information processing section 13 (Step S1). Then, the background of the luminance reversion image is corrected (Step S2).

The background correction may be achieved by preliminarily storing blank image data obtained by luminance reversion of a dark field illumination image captured without the passage of the particles in the memory and comparing the data of the captured image of the particles (luminance reversion image data) with the blank image data.

Subsequently, an edge enhancement operation is performed as pre-processing for accurately extracting particle images (from the luminance reversion image) (Step S3).

More specifically, a generally well known Laplacian enhancement process is performed.

Then, the image data is binarized on the basis of a proper threshold level (Step S4). In turn, it is judged whether a particular point in the binarized image is an edge point of a particle image, and information (i.e., chain codes) indicative of a directional relationship of an adjacent edge point with respect to the particular edge point is generated (Step S5).

Subsequently, edges of particle images are traced with reference to the chain codes, and a total pixel number of each of the particle images (in the luminance reversion image) and positional information of each pixel in the particle images are computed and stored in the memory (Step S6).

Then, it is judged for each of the particle images whether the particle image has a total pixel number of not smaller than 4 (whether the particle has a particle diameter of not smaller than 0.9 μm) (Step S7). For particle images each having a total pixel number of smaller than 4 (particles each having a particle diameter of smaller than 0.9 μm), the dark field illumination image stored in the memory of the information processing section 13 is read out, and particle images in the dark field illumination image are each extracted on the basis of the positional information of the particle images in the luminance reversion image and stored in the memory of the information processing section 13 (Step S8). Then, the routine goes to Step S9 for judging whether the image pickup is to be ended. If the particle image has a total pixel number of not smaller than 4 (the particle has a particle diameter of not smaller than 0.9 μm), the routine also goes to Step S9. If the image pickup is not ended in Step S9, the routine returns to Step S1. If the image pickup is ended, the routine goes to Step S10.

In Step S10, the particle images in the dark field illumination image are read out of the memory of the information processing section 13, and the luminances of the respective pixels constituting each of the particle images are summed on the basis of the positional information of the respective particle images in the luminance reversion image. More specifically, the first computing section 16 calculates the sum bt of the luminances $b_1$, $b_2$, ... $b_n$ of the pixels of each of the particle images (Step S10).

$$bt = b_1 + b_2 + \ldots + b_n \quad (1)$$

Then, a particle diameter D is calculated from the following expression which indicates a relationship between the total luminance value bt and the particle diameter D (Step S11).

$$D = f(bt) \quad (2)$$

In turn, particle size frequency data is prepared on the basis of the particle diameters thus calculated (Step S12). Then, a particle size distribution is prepared on the basis of the particle size frequency data (Step S13).

Thus, the particle size distribution for the particles each having a total pixel number of smaller than 4 is prepared by the first computing section 16.

Next, a process for processing the data of the image captured by the second camera 10 will be described with reference to a flow chart shown in FIG. 5. A bright field illumination image of the particles is first captured by the second camera 10. Then, the captured bright field illumination image is stored in the memory of the information processing section 13 (Step S21). In turn, the background of the bright field illumination image is corrected (Step S22).

The background correction may be achieved by preliminarily storing blank image data obtained by illumination without passage of the particles and comparing the data of the captured image of the particles with the blank image data. Subsequently, an edge enhancement operation is performed as pre-processing for accurately extracting particle images (Step S23). More specifically, a generally well known Laplacian enhancement process is performed.

Then, the image data is binarized on the basis of a proper threshold level (Step S24). In turn, it is judged whether a particular point in the binarized image is an edge point of a particle image, and information (i.e., chain codes) indicative of a directional relationship of an adjacent edge point with respect to the particular edge point is generated (Step S25). Subsequently, edges of particle images are traced with reference to the chain codes, and a total pixel number of each of the particle images is computed and stored in the memory (Step S26).

Then, it is judged for each of the particle images whether the particle image has a total pixel number of not smaller than 4 (whether the particle has a diameter of not smaller than 0.9 μm) (Step S27). For particle images each having a total pixel number of not smaller than 4 (particles each having a diameter of not smaller than 0.9 μm), the total pixel numbers are read out of the memory of the information processing section 13, and stored in correspondence with the respective particle images in the memory of the information processing section 13 (Step S28). Then, the routine goes to Step S29 for judging whether the image pickup is to be ended. If the particle images each have a total pixel number of smaller than 4 (the particles each have a diameter of smaller than 0.9 μm), the routine goes to Step S29. If the image pickup is not ended in Step S29, the routine returns to Step S21. If the image pickup is ended, the routine goes to Step S30.

In Step S30, a particle diameter is calculated on the basis of the total pixel number of each of the particle images. More specifically, the second computing section 17 calculates the projection area S of each of the particles on the basis of the total pixel number nt of the corresponding particle image.

$$S = k \cdot nt \text{ (wherein k is a constant)} \quad (3)$$

Then, a spherical equivalent diameter D is calculated from the following expression (Step S30).

$$D = 2(S/\pi)^{1/2} \quad (4)$$

Then, particle size frequency data is prepared on the basis of the particle diameters thus calculated (Step S31). A particle size distribution is prepared on the basis of the particle size frequency data (Step S32).

Thus, the particle size distribution for the particles each having a total pixel number of not smaller than 4 is prepared by the second computing section 17.

Subsequently, the information processing section 13 combines the particle size distributions prepared by the first computing section 16 and the second computing section 17, and the resulting particle size distribution is outputted to the output section 14.

Here, the expression (2) for calculating the particle diameter on the basis of the luminances of the pixels of each of the particle images in the dark field illumination image is preliminarily determined before the measurement, because the expression (2) is influenced by the light intensity of the light source 1 of the illumination system, the structure of the flow cell 5 and the magnification of the objective lens 6.

Figure 6:
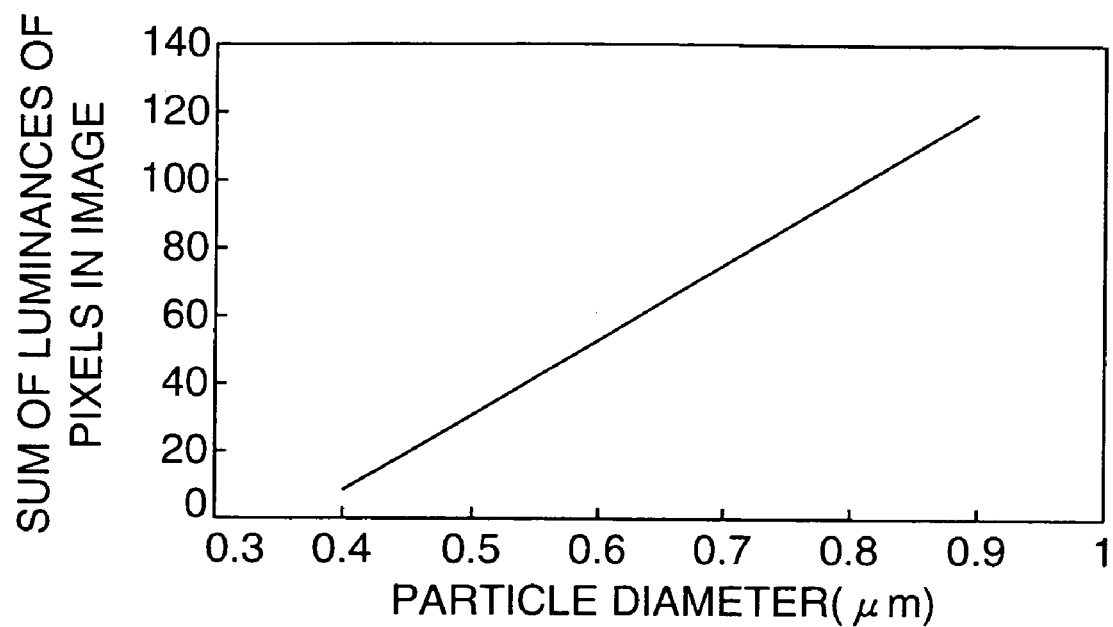
FIG. 6 is a graph illustrating a relationship between the sum of luminances of pixels of an image and a particle diameter.

FIG. 6 is a graph illustrating a relationship between the particle diameter D determined according to Steps S2 to S7 and the sum bt of the luminances of pixels of each particle image when a suspension liquid containing latex particles each having a known particle diameter (0.4 to 0.9 μm) is passed through the flow cell 5 and an image is captured by the first camera 9.

In FIG. 6, the expression (2) is a linear expression of the following monotonously increasing function in a range of $0.4 \leq D \leq 0.9$.

$$D = a \cdot (bt) + c \text{ (wherein a, c are constants)} \quad (5)$$

In this embodiment, the relationship between the particle diameter and the luminance of the particle image for particles having diameters within the range of 0.4 to 0.9 μm is dependent on the monotonously increasing function, so that the calculation is based on the image captured by the first camera 9. The relationship between the particle diameter and the luminance of the particle image for particles having diameters greater than 0.9 μm is not dependent on the monotonously increasing function, so that the calculation is based on the image captured by the second camera 10.

In this embodiment, a total pixel number of 4 is equivalent to a particle diameter of 0.9 μm. If a higher resolution optical system and a higher resolution CCD camera are employed, a total pixel number of 4 is equivalent to a smaller particle diameter. This makes it possible to determine the particle diameter of a smaller particle.

In this embodiment, the luminance reversion image is prepared by reversing the luminance of the dark field illumination image for the image processing. However, the image processing may be performed by employing the dark field illumination image.

Second Embodiment

Figure 7:
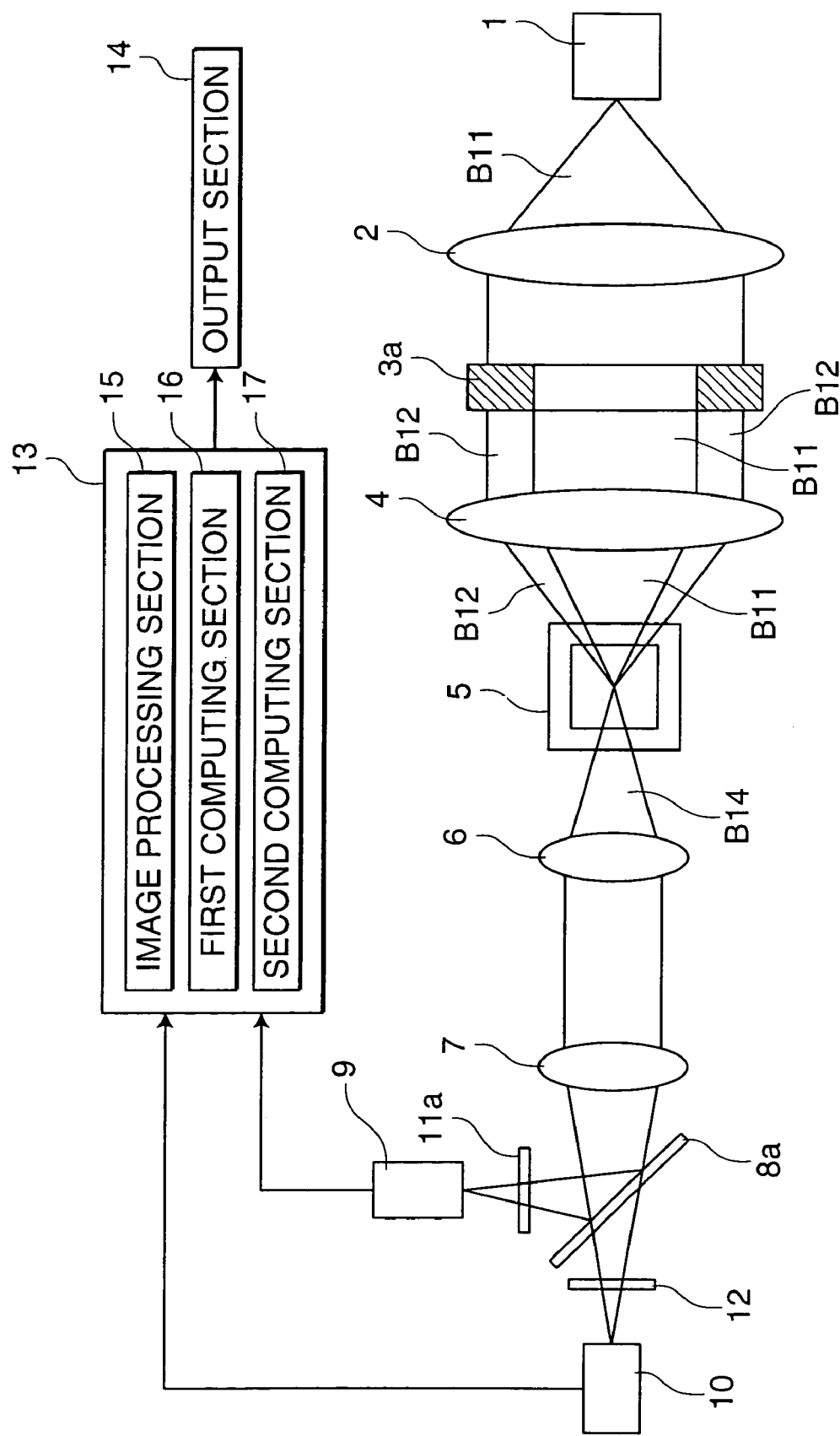
FIG. 7 is a diagram illustrating a construction according to a second embodiment.

FIG. 7 is a diagram illustrating the construction of a particle diameter measuring apparatus according to a second embodiment.

The apparatus according to this embodiment has substantially the same construction as the apparatus according to the first embodiment shown in FIG. 3, except that a filter 3a, an infrared blocking filter 11a and a half mirror 8a are employed instead of the filter 3, the filter 11 and the dichroic mirror 8, respectively, and an infrared transmitting filter 12 is additionally provided between the half mirror 8a and the second camera 10.

The filter 3a is a ring-shaped infrared blocking filter having an opening at its center. That is, the filter blocks infrared light and permits transmission of visible light at its peripheral portion around the opening.

An explanation will be given to an image pickup operation to be performed in this apparatus.

When a suspension liquid containing particles to be subjected to the measurement is caused to flow through the flow cell 5, the control section controls the driving electric power from the driving power source to cause the strobe lamp 1 to emit light in a predetermined cycle. Light B11 emitted from the strobe lamp 1 is converted into parallel light by the collimator lens 2. The condenser lens 4 concentrates light passing through the peripheral portion of the filter 3a around the opening (i.e., light B12) on the flow cell 5, so that the particles flowing through the flow cell 5 are dark-field-illuminated against the objective lens 6.

Further, the condenser lens 4 concentrates light passing through the center opening of the filter 3a (i.e., the light B11 containing the infrared light and the visible light) on the flow cell 5, so that the particles flowing through the flow cell 5 are bright-field-illuminated against the objective lens 6. Light B14 containing infrared light and visible light from the particles is incident on the condenser lens 7 through the objective lens 6.

A half of the light from the condenser lens 7 is reflected on the half mirror 8a, and passes through the infrared blocking filter 11a to be incident on the first camera 9. That is, only the visible light from the particles dark-field-illuminated with the visible light B12 is incident on the first camera 9. Therefore, the first camera 9 captures a dark field illumination image of the particles.

The other half of the light from the condenser lens 7 passes through the half mirror 8a to be incident on the second camera 10 through the filter 12.

That is, only the infrared light out of the light from the particles bright-field-illuminated with the light B11 is incident on the second camera 10. Therefore, the second camera 10 captures a bright field illumination image of the particles.

Figure 4:
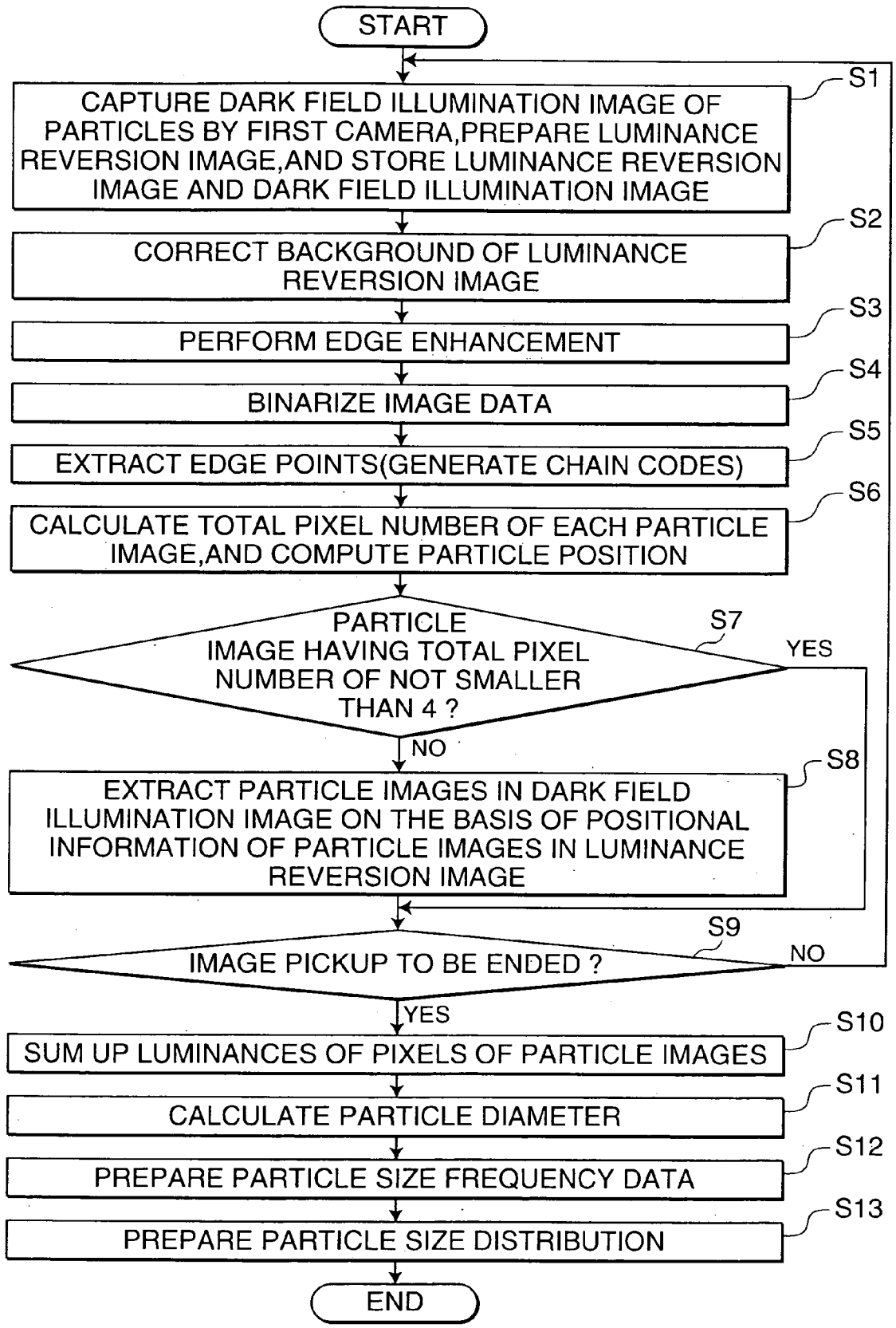
FIG. 4 is a flow chart of a processing operation according to the first embodiment.
Figure 5:
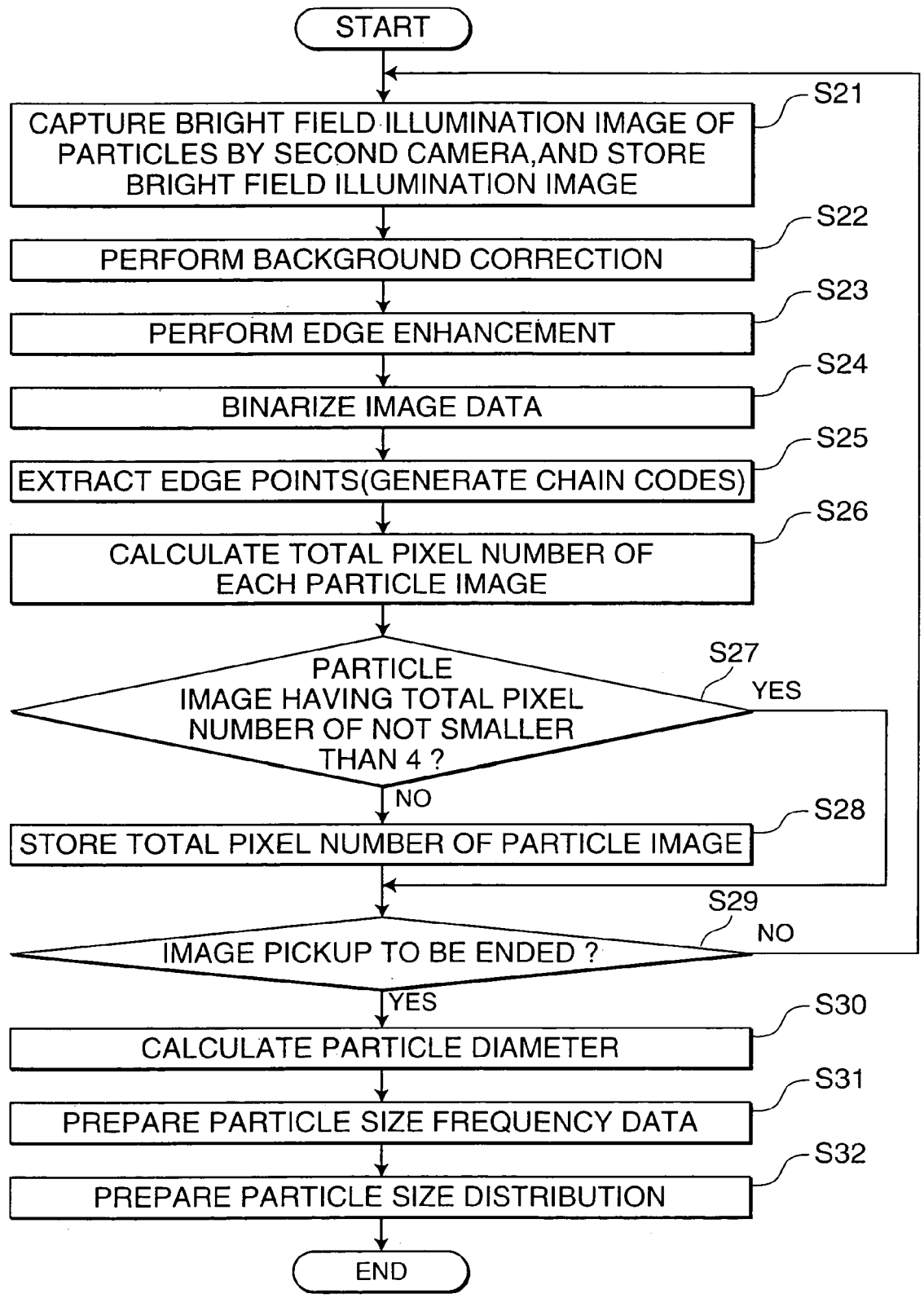
FIG. 5 is a flow chart of another processing operation according to the first embodiment.

Processes for processing the images captured by the first and second cameras 9, 10 are performed in the same manner as shown in FIGS. 4 and 5. The relationship between the particle diameter D and the sum bt of the luminances of the pixels indicated by the expression (2) is preferably preliminarily determined.

Third Embodiment

Figure 8:
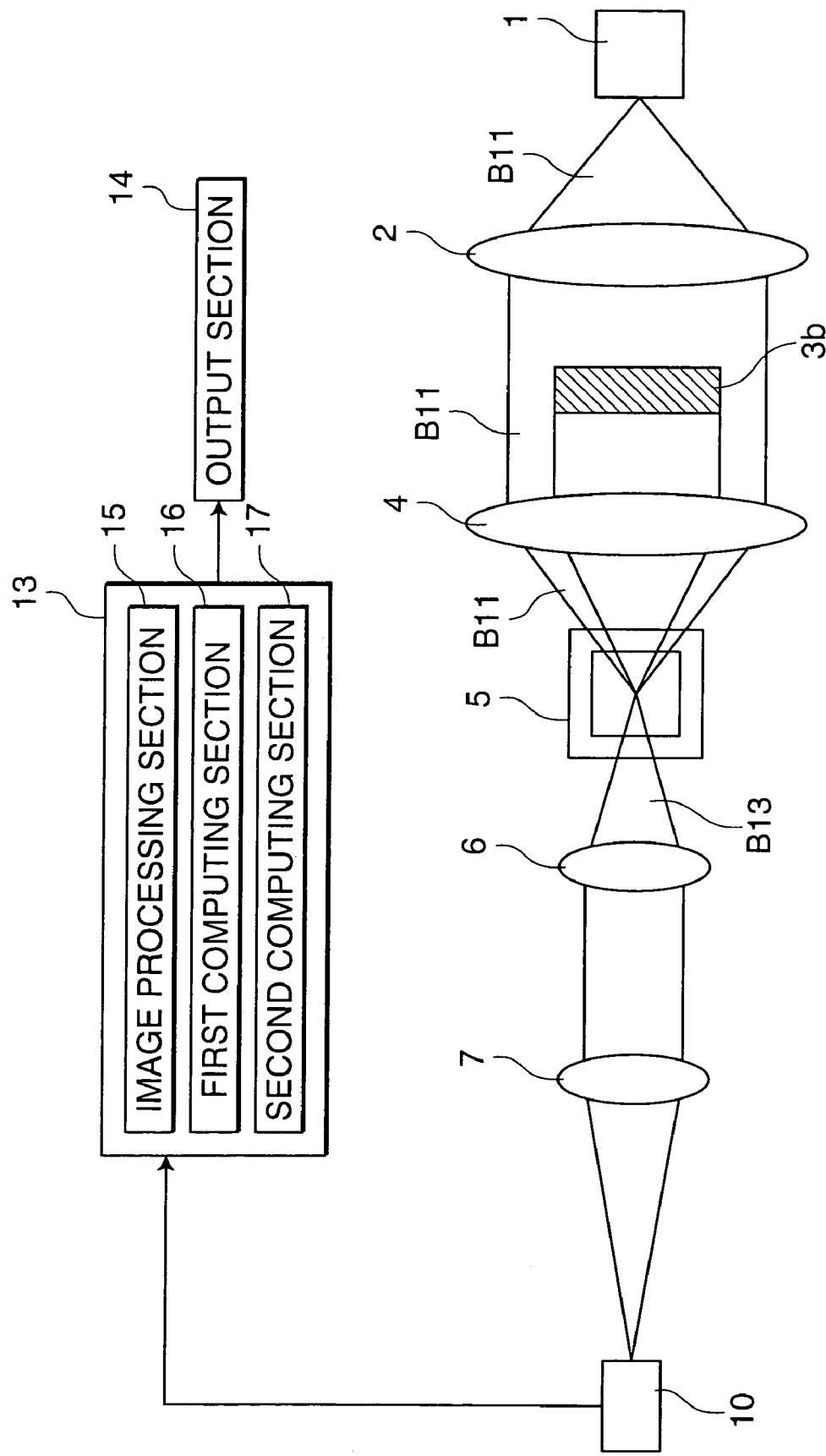
FIG. 8 is a diagram illustrating a construction according to a third embodiment.

FIG. 8 is a diagram illustrating the construction of a particle diameter measuring apparatus according to a third embodiment. The apparatus according to this embodiment has substantially the same construction as the apparatus according to the first embodiment shown in FIG. 3, except that a light blocking plate 3b is provided instead of the filter 3 and the filter 11, the dichroic mirror 8, the first camera 11 and the visible light B12 are omitted.

An explanation will be given to an image pickup operation to be performed in this apparatus. When a suspension liquid containing particles to be subjected to the measurement is caused to flow through the flow cell 5, the strobe lamp 1 emits light in a predetermined cycle. Light B11 emitted from the strobe lamp 1 is converted into parallel light by the collimator lens 2. The condenser lens 4 concentrates light traveling outside the light blocking plate 3b on the flow cell 5, so that the particles flowing through the flow cell 5 are dark-field-illuminated against the objective lens 6.

Light B13 from the particles is incident on the condenser lens 7 through the objective lens 6. A dark field illumination image of the particles formed by light from the condenser lens 7 is captured by the second camera 10.

Next, a process for processing data of the image captured by the second camera 10 will be described.

A dark field illumination image of the particles is first captured by the second camera 10. Then, the captured dark field illumination image is converted into a luminance reversion image, which is in turn stored together with the dark field illumination image in the memory of the information processing section 13. Then, the background of the luminance reversion image is corrected.

The background correction may be achieved by preliminarily storing blank image data obtained by luminance reversion of a dark field illumination image captured without passage of the particles in the memory and comparing the data of the captured image of the particles (luminance reversion image data) with the blank image data. Subsequently, an edge enhancement operation is performed as pre-processing for accurately extracting particle images (from the luminance reversion image). More specifically, a generally well known Laplacian enhancement process is performed.

Then, the image data is binarized on the basis of a proper threshold level. In turn, it is judged whether a particular point in the binarized image is an edge point of a particle image, and information (i.e., chain codes) indicative of a directional relationship of an adjacent edge point with respect to the particular edge point is generated. Subsequently, edges of particle images are traced with reference to the chain codes, and a total pixel number of each of the particle images (in the luminance reversion image) and positional information of each pixel in the particle images are computed and stored in the memory.

Then, it is judged for each of the particle images whether the particle image has a total pixel number of not smaller than 4 (whether the particle has a particle diameter of not smaller than 0.9 μm). For particle images each having a total pixel number of smaller than 4 (particles each having a diameter of smaller than 0.9 μm), the dark field illumination image stored in the memory of the information processing section 13 is read out, and particle images in the dark field illumination image are each extracted on the basis of the positional information of the particle images in the luminance reversion image and stored in the memory of the information processing section 13.

For particle images each having a total pixel number of not smaller than 4 (particles each having a diameter of not smaller than 0.9 μm), the total pixel numbers are read out of the memory of the information processing section 13, and stored in correspondence with the respective particle images in the memory of the information processing section 13.

Then, it is judged whether the image pickup is to be performed. If the image pickup is not ended, a dark field illumination image of particles is captured again. If the image pickup is ended, different processes are performed in the case where the total pixel number of the particle image is not smaller than 4 (the particle has a diameter of not smaller than 0.9 μm) and in the case where the total pixel number of the particle image is smaller than 4 (the particle has a diameter of smaller than 0.9 μm)

For particle images each having a total pixel number of smaller than 4 (particles each having a diameter of smaller than 0.9 μm), the dark field illumination image for the particles is read out of the memory of the information processing section 13, and the luminances of the respective pixels constituting each of the particle images are summed on the basis of the positional information of the respective particle images in the luminance reversion image for calculation of a particle diameter. More specifically, the first computing section 16 calculates the particle diameter from the expressions (1) and (2) described above.

In turn, particle size frequency data is prepared on the basis of the particle diameters thus calculated. Then, a particle size distribution is prepared on the basis of the particle size frequency data.

Thus, the particle size distribution for the particles each having a total pixel number of smaller than 4 is prepared by the first computing section 16.

For the particle images each having a total pixel number of not smaller than 4 (the particles each having a diameter of not smaller than 0.9 μm), the total pixel number for each of the particle images is read out of the memory of the information processing section 13, and the particle diameter is calculated on the basis of the total pixel number of the particle image. More specifically, the second computing section 17 calculates the particle diameter from the expressions (3) and (4) described above.

In turn, particle size frequency data is prepared on the basis of the particle diameters thus calculated. Then, a particle size distribution is prepared on the basis of the particle size frequency data.

Thus, the particle size distribution for the particles each having a total pixel number of not smaller than 4 is prepared by the second computing section 17.

In turn, the information processing section 13 combines the particle size distributions prepared by the first computing section 16 and the second computing section 17, and the resulting particle size distribution is outputted to the output section 14.

Examples of the particles to be subjected to the measurement include solid constituents of blood and urine, inorganic particles such as fine ceramic particles, pigment particles, cosmetic particles, toner particles, abrasive particles and carbon nanotubes, and organic particles such as food additive particles.

CCD cameras are preferably employed as the first camera 9 and the second camera 10. The first and second computing sections 16, 17 may comprise a microprocessor or a personal computer comprising a CPU, a ROM and a RAM.

What is claimed is:

1. A particle diameter measuring apparatus comprising:
   a dark field illumination section which dark-field-illuminates particles;
   an image pickup section which captures a particle image of each of the dark-field-illuminated particles;
   a first computing section which calculates a particle diameter of each particle based on luminance of the captured particle image; and
   a second computing section which calculates the particle diameter on the basis of a morphological characteristic of the captured particle image.

2. A particle diameter measuring apparatus as set forth in claim 1, wherein the first computing section calculates the particle diameter based on the luminance of the particle image from a monotonously increasing function.

3. A particle diameter measuring apparatus as set forth in claim 1, wherein the first computing section calculates the particle diameter based on the luminance of the captured particle image if the particle image has a total pixel number smaller than a predetermined value, and the second computing section calculates the particle diameter on the basis of the morphological characteristic of the captured particle image if the particle image has a total pixel number not smaller than the predetermined value.

4. A particle diameter measuring apparatus as set forth in claim 3, wherein the morphological characteristic is an area.

5. A particle diameter measuring apparatus as set forth in claim 1, further comprising a flow cell through which a suspension liquid containing particles is passed.

6. A particle diameter measuring apparatus as set forth in claim 1, wherein the image pickup section comprises a two-dimensional image pickup device.

7. A particle diameter measuring apparatus as set forth in claim 1, wherein the dark field illumination section comprises a light source which illuminates the particles, and a light blocking member provided in a light path extending from the light source to the particles for blocking light traveling along and around an optical axis thereof.

8. A particle diameter measuring apparatus comprising:
   a dark field illumination section which dark-field-illuminates particles;

a first image pickup device which captures a particle image of each of the dark-field-illuminated particles;

a first computing section which calculates a particle diameter of each particle on the basis of luminance of the particle image captured by the first image pickup device;

a bright field illumination section which bright-field-illuminates the particles;

a second image pickup device which captures a particle image of each of the bright-field-illuminated particles; and a second computing section which calculates the particle diameter on the basis of a morphological characteristic of the particle image captured by the second image pickup device.

9. A particle diameter measuring apparatus as set forth in claim 8, wherein the first computing section calculates the particle diameter if the captured particle image has a total pixel number smaller than a predetermined value, and the second computing section calculates the particle diameter if the captured particle image has a total pixel number not smaller than the predetermined value.

10. A particle diameter measuring apparatus as set forth in claim 8, wherein the first computing section calculates the particle diameter on the basis of the luminance of the particle image captured by the first image pickup device from a monotonously increasing function.

11. A particle diameter measuring apparatus as set forth in claim 8, wherein the second computing section calculates the particle diameter on the basis of an area of the particle image captured by the second image pickup device.

12. A particle diameter measuring apparatus as set forth in claim 8, further comprising a flow cell through which a suspension liquid containing particles is passed.

13. A particle diameter measuring apparatus as set forth in claim 8, wherein the first and second image pickup devices each comprise a two-dimensional image pickup device.

14. A particle diameter measuring apparatus comprising:

a light source for illuminating particles;

a first filter provided in a light path extending from the light source to the particles for blocking light of a predetermined wavelength traveling along and around an optical axis thereof;

first optical means which illuminates the particles with light passing through the first filter and with light traveling outside the first filter;

second optical means which divides light from the illuminated particles into two light components;

a first image pickup device which captures a particle image of each of the particles by one of the light components divided by the second optical means;

a second image pickup device which captures a particle image of each of the particles by the other light component divided by the second optical means; and a second filter disposed in a light path extending between the second optical means and the first image pickup device and transmitting only the light of the predetermined wavelength.

15. A particle diameter measuring apparatus as set forth in claim 14, wherein the particles are dark-field-illuminated with light traveling outside the first filter, and are bright-field-illuminated with light passing through the first filter.

16. A particle diameter measuring apparatus as set forth in claim 14, further comprising a first computing section which calculates a particle diameter on the basis of luminance of the particle image captured by the first image pickup device, and a second computing section which calculates the particle diameter on the basis of a morphological characteristic of the particle image captured by the second image pickup device.

17. A particle diameter measuring apparatus as set forth in claim 16, wherein the first computing section calculates the particle diameter if the captured particle image has a total pixel number smaller than a predetermined value, and the second computing section calculates the particle diameter if the captured particle image has a total pixel number not smaller than the predetermined value.

18. A particle diameter measuring apparatus as set forth in claim 16, wherein the first computing section calculates the particle diameter on the basis of the luminance of the particle image captured by the first image pickup device from a monotonously increasing function.

19. A particle diameter measuring apparatus as set forth in claim 16, wherein the second computing section calculates the particle diameter on the basis of an area of the particle image captured by the second image pickup device.

* * * * *